(12) United States Patent
Bechard et al.

(10) Patent No.: US 8,678,649 B2
(45) Date of Patent: Mar. 25, 2014

(54) CONVERSION OF EXISTING PORTABLE OR MOBILE ANALOG RADIOGRAPHIC APPARATUS FOR ENABLING DIGITAL RADIOGRAPHIC APPLICATIONS

(75) Inventors: Brian J. Bechard, Syracuse, NY (US); Thomas W. Rosevear, East Syracuse, NY (US); Bruce A. Perry, Fulton, NY (US)

(73) Assignee: Varian Medical Systems, Inc., Palo Alto, CA (US)

( * ) Notice: Subject to any disclaimer, the term of this patent is extended or adjusted under 35 U.S.C. 154(b) by 280 days.

(21) Appl. No.: 13/169,628

(22) Filed: Jun. 27, 2011

(65) Prior Publication Data

US 2011/0317816 A1 Dec. 29, 2011

Related U.S. Application Data

(60) Provisional application No. 61/358,660, filed on Jun. 25, 2010.

(51) Int. Cl.
*H05G 1/02* (2006.01)

(52) U.S. Cl.
USPC .......................................................... 378/198

(58) Field of Classification Search
USPC ................... 378/62, 198, 98.8, 114–116, 197
See application file for complete search history.

(56) References Cited

U.S. PATENT DOCUMENTS

| | | |
|---|---|---|
| 5,499,284 A | 3/1996 | Pellegrino et al. |
| 5,835,558 A | 11/1998 | Maschke |
| 5,901,200 A | 5/1999 | Krause |
| 6,183,417 B1 | 2/2001 | Gehab et al. |
| 6,409,382 B1 | 6/2002 | Akutsu et al. |
| 6,594,146 B2 | 7/2003 | Frangesch et al. |
| 6,702,459 B2 | 3/2004 | Barnes et al. |
| 6,856,506 B2 | 2/2005 | Doherty et al. |
| 7,006,600 B1 | 2/2006 | Krema et al. |
| 7,016,467 B2 | 3/2006 | Brooks |

(Continued)

FOREIGN PATENT DOCUMENTS

| | | |
|---|---|---|
| JP | H11-104127 A | 4/1999 |
| JP | 2007-000535 A | 1/2007 |
| WO | 2007/098920 A2 | 9/2007 |
| WO | 2009/067189 A1 | 5/2009 |

OTHER PUBLICATIONS

International Search Report/Written Opinion for PCT Application No. PCT/US2011/042010; mailed Feb. 9, 2012; 7 pages.

(Continued)

*Primary Examiner* — Courtney Thomas
(74) *Attorney, Agent, or Firm* — Vista IP Law Group, LLP

(57) ABSTRACT

A kit for converting an existing mobile or portable film X-ray examination apparatus typically configured solely for analog radiography to enable said examination apparatus for digital radiographic applications. The kit includes a tablet PC that is attached to the wheeled chassis of the mobile or portable apparatus, and an input/output device used to divert the exposure control signal from the user actuable exposure control switch of the apparatus to the tablet PC. The tablet PC includes image processing software that controls the operation of a digital flat panel detector. The tablet PC can further be used to separately control other mobile or portable apparatus or a facility or examination room that was previously configured only for analog radiography.

22 Claims, 16 Drawing Sheets

(56) References Cited

U.S. PATENT DOCUMENTS

| | | |
|---|---|---|
| 7,311,657 B2 | 12/2007 | Boone et al. |
| 2002/0082479 A1 | 6/2002 | Frangesch et al. |
| 2004/0146142 A1 | 7/2004 | Maijala |
| 2005/0053199 A1 | 3/2005 | Miles |
| 2006/0034427 A1 | 2/2006 | Brooks |
| 2006/0070384 A1 | 4/2006 | Ertel |
| 2007/0153980 A1 | 7/2007 | Butzine et al. |
| 2008/0003989 A1 | 1/2008 | Vau et al. |
| 2008/0020332 A1 | 1/2008 | Lavenda et al. |
| 2008/0048124 A1 | 2/2008 | Pang et al. |
| 2008/0110460 A1 | 5/2008 | Elaz et al. |
| 2008/0144777 A1 | 6/2008 | Wilson |
| 2009/0014661 A1 | 1/2009 | Yagi et al. |
| 2009/0103679 A1 | 4/2009 | Jabri et al. |
| 2011/0123001 A1* | 5/2011 | Kopcienski et al. .......... 378/198 |

OTHER PUBLICATIONS

International Preliminary Report on Patentability dated Dec. 28, 2012 for PCT Patent Application No. PCT/US2011/042010.

Notice of Reasons for Rejection dated Jan. 7, 2014, for related Japanese Patent Application No. 2013-516851, 7 pages.

* cited by examiner

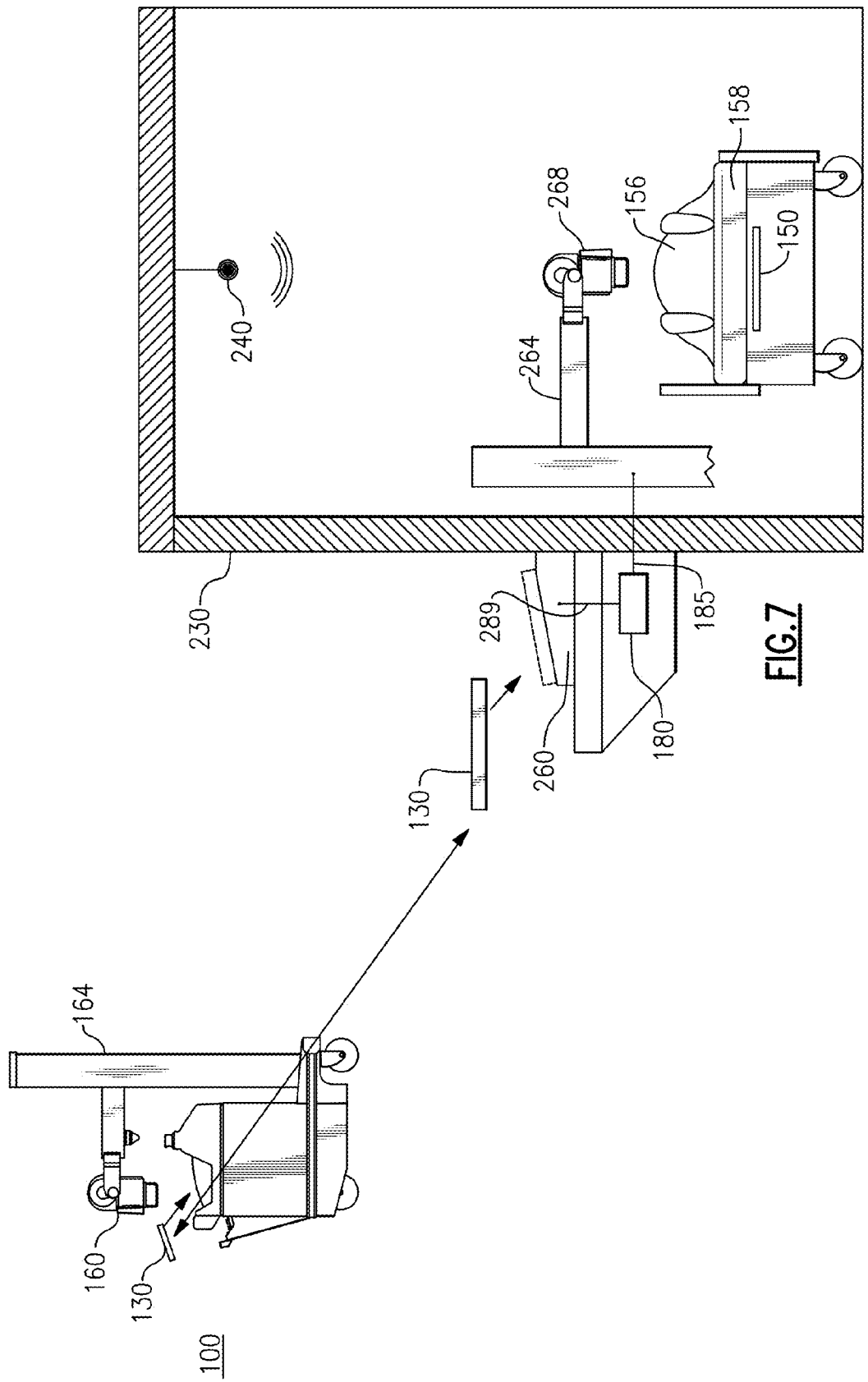

FIG. 15

CONVERSION OF EXISTING PORTABLE OR MOBILE ANALOG RADIOGRAPHIC APPARATUS FOR ENABLING DIGITAL RADIOGRAPHIC APPLICATIONS

CROSS REFERENCE TO RELATED APPLICATION

Pursuant to applicable paragraphs of 35 U.S.C. §119, this application is based upon a provisional patent application U.S. Ser. No. 61/358,660, filed Jun. 25, 2010, and entitled: DIGITAL RADIOGRAPHIC APPARATUS AND RELATED METHOD OF USE, the entire contents of which are herein incorporated by reference.

BACKGROUND

X-ray apparatus are commonly known in the field of diagnostic medicine, and are utilized for a varied number of medical examination procedures. Certain X-ray apparatus are dedicated to a specified area or a medical examination room in which patients are brought for a specified examination procedure(s). These apparatus are typically provided as dedicated hardware that is fixedly mounted within the specified area(s) or medical examination room(s) of the facility to which the patient is brought. Alternatively, there are other known X-ray apparatus that are either mobile or portable. Mobile X-ray examination apparatus are typically defined by a wheeled chassis or cart having an X-ray generator mounted thereon in which the apparatus can be moved as needed between rooms or other areas within a hospital or other medical facility, providing more flexibility than fixed apparatus versions. Portable X-ray examination apparatus are somewhat more compact than the mobile apparatus versions noted above, the latter diagnostic apparatus being characterized by a foldable form of wheeled structure that enables movement in and out of a medical facility so as to enable X-ray examinations to be conducted remotely, thereby providing yet another level of versatility in enabling certain X-ray examinations to take made, as needed.

Each of the above-noted types of X-ray apparatus are well known for purposes of incorporating analog or film-based radiography, in which each apparatus relies upon X-ray film or individual film cassettes that must be replaced following each exposure and further requiring that an available supply or inventory of film or film cassettes be continually maintained. Use of X-ray film or film cassettes requires precision in their alignment between the X-ray source and the cassette/film in order to obtain an acceptable image. In addition, each individual X-ray exposure that is taken using analog film and/or film cassettes must be separately removed from the examination room in which the exposure is taken and subsequently placed on a light table or similar apparatus for analysis/review, requiring additional time and effort.

More recent advances to X-ray diagnostic equipment have been made in the field of digital radiography, providing benefits through the use of digital flat panel detectors in lieu of a supply of traditional film and/or film cassettes. Advantageously, digital flat panel detectors such as those sold by Carestream Health, Varian, Samsung and GE Medical Systems, among others, can be used in real time and do not require replacement following each exposure such that a single digital flat panel detector, based on a single charge of a contained detector battery, can be continuously used for the acquisition of multiple exposures, thereby increasing throughput as well as being time and cost effective in terms of their implementation and use. Typically, digital flat panel detectors are connected to X-ray generation equipment through either wired and/or wireless communication techniques.

It is a general desire in the medical diagnostic field to be able to upgrade or retrofit existing film-based (analog) X-ray diagnostic apparatus in order to enable digital radiography capability and thereby provide enhanced and improved versatility to patients and caregivers in a hospital or other medical facility. Specific mobile and portable x-ray diagnostic apparatus are presently available that are already configured for digital radiography. However, wholesale conversions or movement into this technology, based on the costs of digital radiographic apparatus in particular, is prohibitively expensive. It is therefore a further general desire in the field to provide such enhancements to existing analog diagnostic apparatus, but without significantly impacting the cost, labor and/or time efforts for making such conversions.

SUMMARY

Therefore and according to one aspect, a mobile or portable X-ray diagnostic apparatus is provided that is originally solely configured for analog-based radiography operation, the mobile or portable diagnostic apparatus including a wheeled chassis or cart having disposed thereon an X-ray generator assembly, said cart including an operator console including a user actuable exposure control switch linked to said X-ray generator assembly, the X-ray apparatus further including a conversion kit for enabling digital radiography, said conversion kit including a tablet PC serving as an user interface in combination with one of the portable and mobile X-ray diagnostic apparatus which is attached to said wheeled cart, and means for enabling the tablet PC to receive an exposure control signal from said user actuable exposure control switch without otherwise interfering with the operation of said X-ray generator assembly, said tablet PC including image processing software for the management of exposures received from a digital flat panel detector.

In a preferred version, the tablet PC is releasably attached to the mobile or portable X-ray diagnostic apparatus. In one exemplary version, a replacement cover is provided for the wheeled cart, the replacement cover having at least one defined receptacle or cavity which is appropriately sized and configured for releasably retaining the tablet PC. In one version, the resident battery of the tablet PC enables operation thereof, but without otherwise impacting or influencing the existing power supply of the mobile or portable diagnostic apparatus. According to another aspect, the apparatus further includes means for storing the tablet PC when the tablet PC is not in use, as well as means for storing at least one digital flat panel detector to facilitate mobile transport of the apparatus. In yet another exemplary version, the apparatus can include switching means linked to the exposure control signal receiving means for permitting the mobile or portable X-ray diagnostic apparatus to be selectively enabled for either analog or digital radiographic operation.

The means for receiving the exposure control signal of the mobile or portable X-ray apparatus according to one version includes an I/O modular intercept box that is either mounted on or within the wheeled cart, the intercept box having suitable circuitry to permit the exposure control signal to be directed to each of the tablet PC and the X-ray generator assembly. The I/O intercept box is preferably retained within a suitably sized recess formed on the replacement cover beneath the receptacle retaining the tablet PC. Other suitable storage configurations will be readily apparent for storing the tablet PC and/or the I/O intercept box in conjunction with the herein described apparatus.

According to another aspect, there is provided a kit for converting a mobile or portable X-ray diagnostic apparatus originally solely configured for analog-based radiography into a digital radiography apparatus, the conversion kit comprising a tablet PC having a user interface and software capable of receiving and otherwise directing the exposure of a digital flat panel detector, and means for directing the user-actuable exposure control signal of said mobile or portable apparatus to said tablet PC.

According to yet another version, the tablet PC is selectively removable from the portable or mobile X-ray diagnostic apparatus allowing the tablet PC to be separately used, for example, using an external wireless access point (WAP) or other wired or wireless communication means, in combination with a docking station to enable an examination room that is previously enabled only for film (analog) radiography to be converted so as to enable digital radiography applications.

According to yet another version, a method is provided for converting a mobile or portable diagnostic X-ray apparatus originally solely configured for analog-based radiography, said apparatus including a wheeled cart including an X-ray generator, a resident power supply, and a user actuable exposure control means for controlling the exposure of X-rays using said generator, said method including the steps of routing the exposure control signal from said user actuable exposure control means of said apparatus to a tablet PC, the tablet PC including resident software for controlling the operation of a digital flat panel detector, and releasably positioning said tablet PC on said wheeled cart to said apparatus to enable operation thereof by said user wherein said routing step is performed using an interface device that is connected with the exposure control circuitry of said apparatus.

According to one described version, power for the tablet PC is maintained solely via its stored battery or alternatively a separate dedicated power supply wherein power consumption of the tablet PC does not in any way siphon from the X-ray generator or its associated electronics. According to one version, a wireless router and wireless access port (WAP) provided on or in the vicinity of the tablet PC or elsewhere on the diagnostic apparatus enables wireless operation with the digital flat panel detector. Alternatively, the tablet PC can be connected to the digital flat panel detector by means of a wired connection.

According to yet another version, the tablet PC can be further used in order to "convert" other examination apparatus of a medical facility from a conventional analog to a digital based platform. For example, an examination room that is originally configured solely for analog X-ray examination can be converted by routing or diverting the user actuated exposure control signal to a tablet PC, the tablet PC being attached, for example, to a docking station immediately outside the examination room and having resident software for digital radiographic operation of a flat panel detector, including calibration thereof, if needed. A wireless router and a wireless access point (WAP) provided as part of the tablet PC or added within the examination room can be used to wirelessly communicate with the digital flat panel detector. A suitably positioned I/O device diverts the exposure control signal to the tablet PC and enables operation and control of digital exposures taken using the X-ray generator and digital flat panel detector. Alternatively, wired connections can be provided between the digital flat panel detector and the tablet PC and/or docking station according to this version.

Unlike other proprietary digitally based software and according to at least one version, the herein described mobile or portable X-ray diagnostic apparatus can interchangeably be used with various digital flat panel detectors.

One advantage realized by the present apparatus and method is increased versatility in a medical facility, wherein existing analog X-ray diagnostic apparatus can be readily converted for purposes of conducting digital radiographic examinations, but without any appreciable or significant impact in terms of cost, labor and/or time.

Yet another advantage realized is that the use of a tablet PC and intercept device provides duality in function to enable mobile/portable X-ray examination apparatus and examination rooms that have previously not been enabled for digital radiography to be easily and effectively converted. For example and according to one version, a single tablet PC could be used, if needed, in conjunction with more than one examination room or mobile or portable apparatus.

These and other features and advantages will be readily apparent from the following Detailed Description, which should be read in conjunction with the accompanying drawings.

BRIEF DESCRIPTION OF THE DRAWINGS

FIG. 7 is a schematic figure illustrating dual functionality of the tablet PC used in the mobile X-ray diagnostic apparatus of FIGS. 1-6, with regard to converting a mobile or transport analog X-ray apparatus and a separate mode; namely, converting an examination room that is previously configured only for analog X-ray examination; and FIGS. 8-15 depict a series of exemplary screenshots taken by the tablet PC of the herein described mobile X-ray diagnostic apparatus, illustrating a user interface including acquisition and review of digital images.

DETAILED DESCRIPTION

Throughout the course of the following discussion, reference is made to various terms in order to provide a suitable frame of reference in regard to the accompanying drawings. These terms, except where so specifically indicated, are not intended to be overlimiting of the inventive concepts provided herein. It should further be noted that the drawings as represented may not necessarily be to scale in order to more clearly depict certain features more clearly.

The following description relates to an exemplary embodiment directed to the conversion of a so-called "mobile" X-ray examination apparatus that is originally solely configured for conventional (analog or film-based) radiography. According to the herein described version, this type of apparatus can easily be upgraded to a digital radiography platform using a digital conversion kit. By way of example for purposes of this specific embodiment, the mobile diagnostic apparatus that is adapted herein is an AMX-4 mobile X-ray cart that is originally sold by GE Medical Products. The selection of this apparatus for purposes of this invention is purely exemplary and it should be readily understood to those of suitable skill that other mobile or portable analog diagnostic X-ray apparatus could be similarly and readily adapted for conversion to digital radiography in the manner that is generally described herein.

Figure 1:
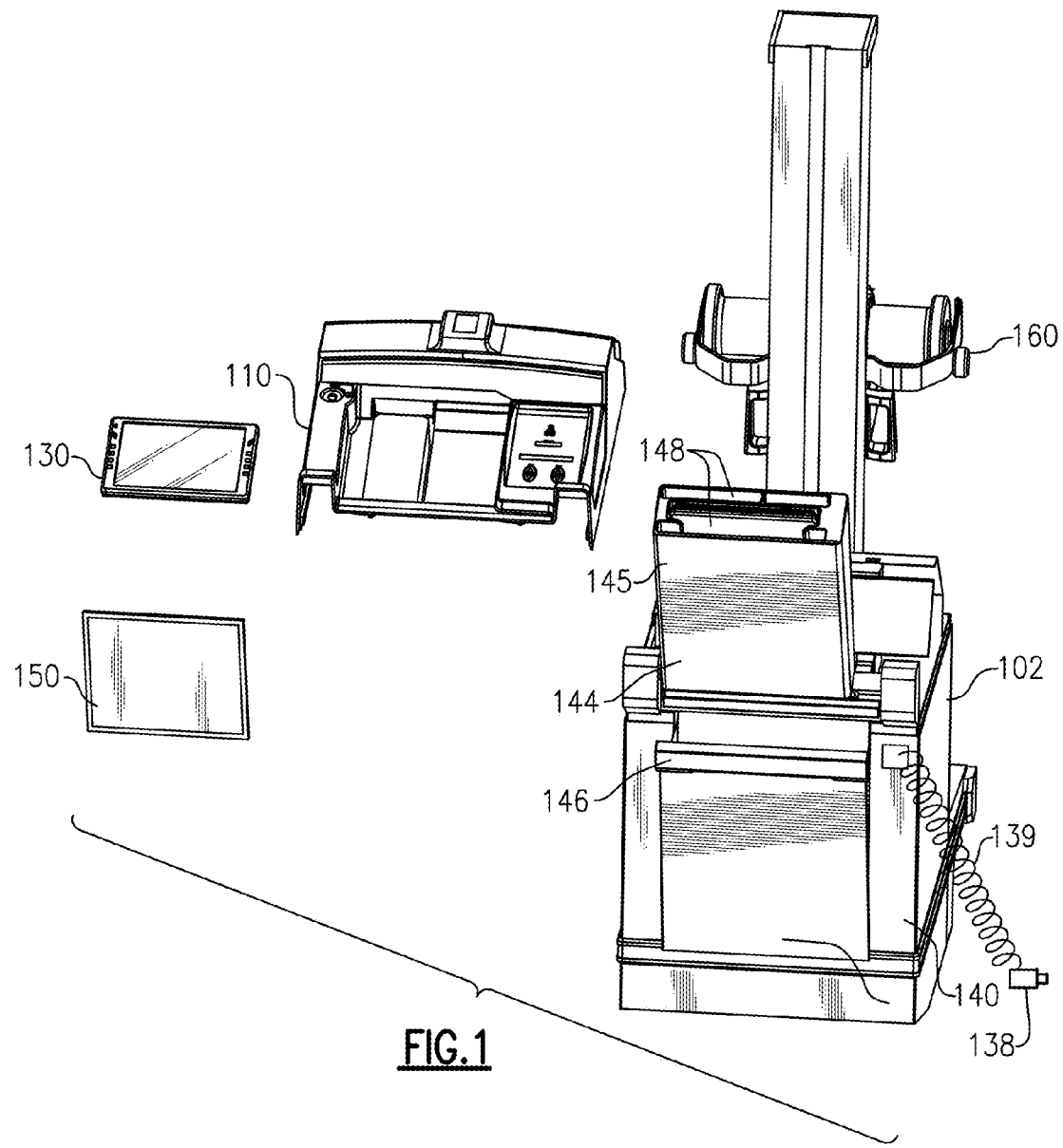
FIG. 1 is a partially exploded assembly view of a mobile analog X-ray diagnostic apparatus, including major components of a conversion kit for enabling the diagnostic apparatus for digital radiographic applications, according to an exemplary embodiment.

As shown in FIG. 1, the mobile X-ray diagnostic apparatus 100 according to this herein described embodiment includes a wheeled cart 102 having an integrated X-ray generator assembly 160 powered by series of various controls that are provided on an operator's console on an original cover 101, including a tethered user actuable exposure control switch 138, and a digital conversion kit 103. The digital conversion kit 103 according to this embodiment includes a tablet PC 130, a replacement cover 110 for the wheeled cart 102, at least one digital flat panel X-ray detector 150, and means, including associated cabling (not shown), for diverting or routing the exposure control signal from the tethered user actuable hand control 138 provided on the wheeled cart 102 to the tablet PC. Additionally and according to this exemplary embodiment, a drawer insert 144 is further provided that is added to the enclosure of the drawer 140 of the wheeled cart 102.

As briefly described herein and according to this embodiment, the original cover 101 (shown only in FIG. 1) of the mobile apparatus 100 is removed from the top of the wheeled cart 102 in lieu of the replacement cover 110, this cover being configured for retaining the tablet PC 130 as well as the exposure control signal diverting or routing means. In addition and according to this embodiment, a wireless router 152, shown diagrammatically in FIG. 5, enables wireless communication between the tablet PC 130 and the digital flat panel detector 150 for controlling the acquisition of X-ray images (exposures). Alternatively or in combination therewith, other hardwired and/or wireless linkages can also be suitably established between the tablet PC 130 and the digital flat panel detector 150.

Figure 2:
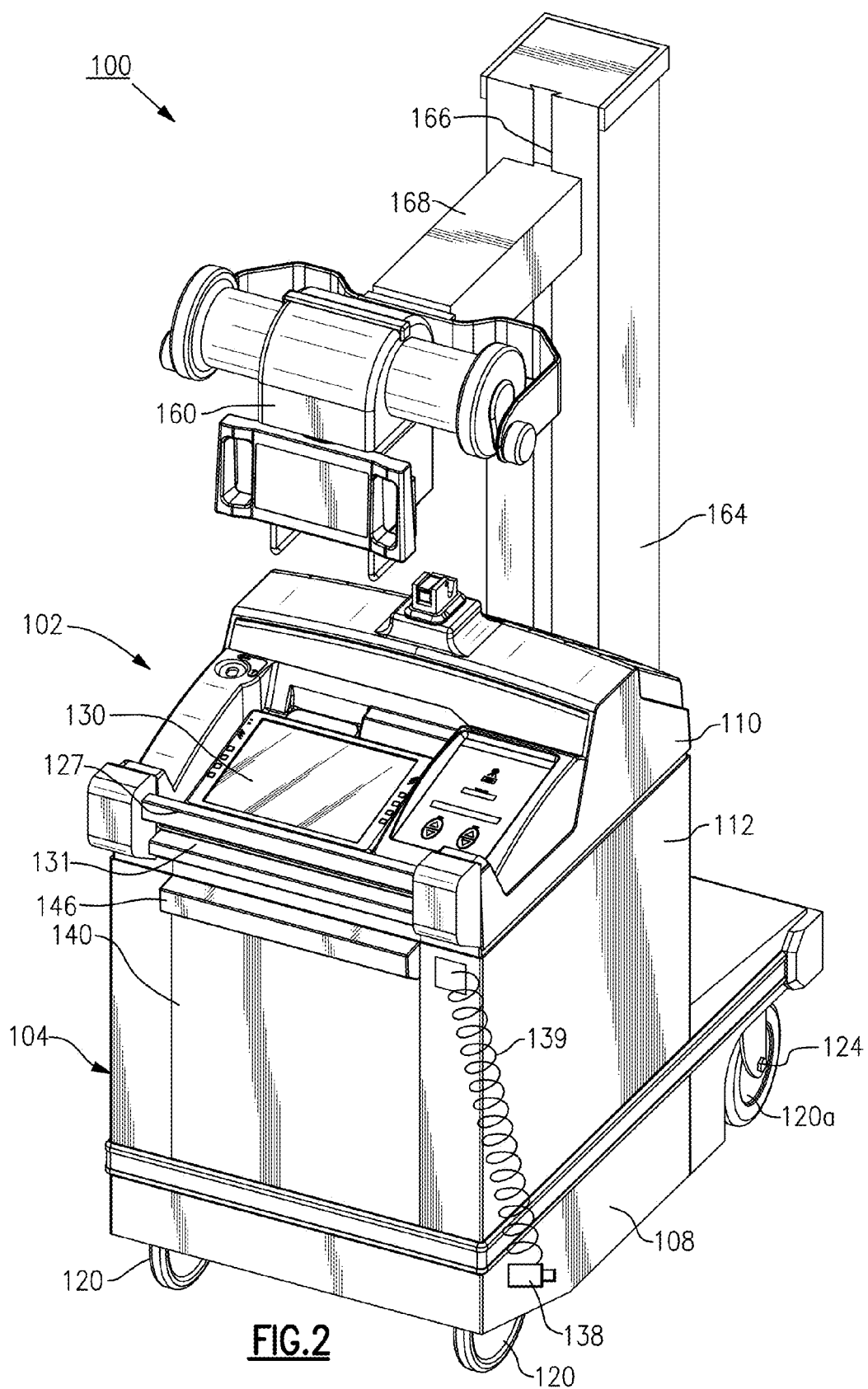
FIG. 2 is a top perspective view of the converted mobile X-ray diagnostic apparatus of FIG. 1.

Referring to FIG. 2, the wheeled cart 102 of the apparatus 100 is defined by a chassis 104 made from aluminum or other suitable material, the chassis being further defined by a base section 108 formed at a lower or bottom end thereof that supports an apparatus portion 112. The apparatus portion 112 of the wheeled cart 102 is sized to retain a plurality of components for purposes of X-ray generation, as discussed below. The cart 102 is further defined by an upper end that supports the original cover 101 of the apparatus 100 and eventually when converted according to this embodiment, the replacement cover 110. The user actuable exposure control switch 138 is tethered by a cord or wire 139 to the front facing side of the cart 102, the exposure control switch being connected to the X-ray generator assembly 160 through associated cabling. Alternatively and in passing, it should be noted that other forms of connection for the exposure control switch can be contemplated, including non-tethered (wireless) versions. Each of these variations are contemplated by the present invention, although the present embodiment relates only to the tethered configuration.

Figure 3:
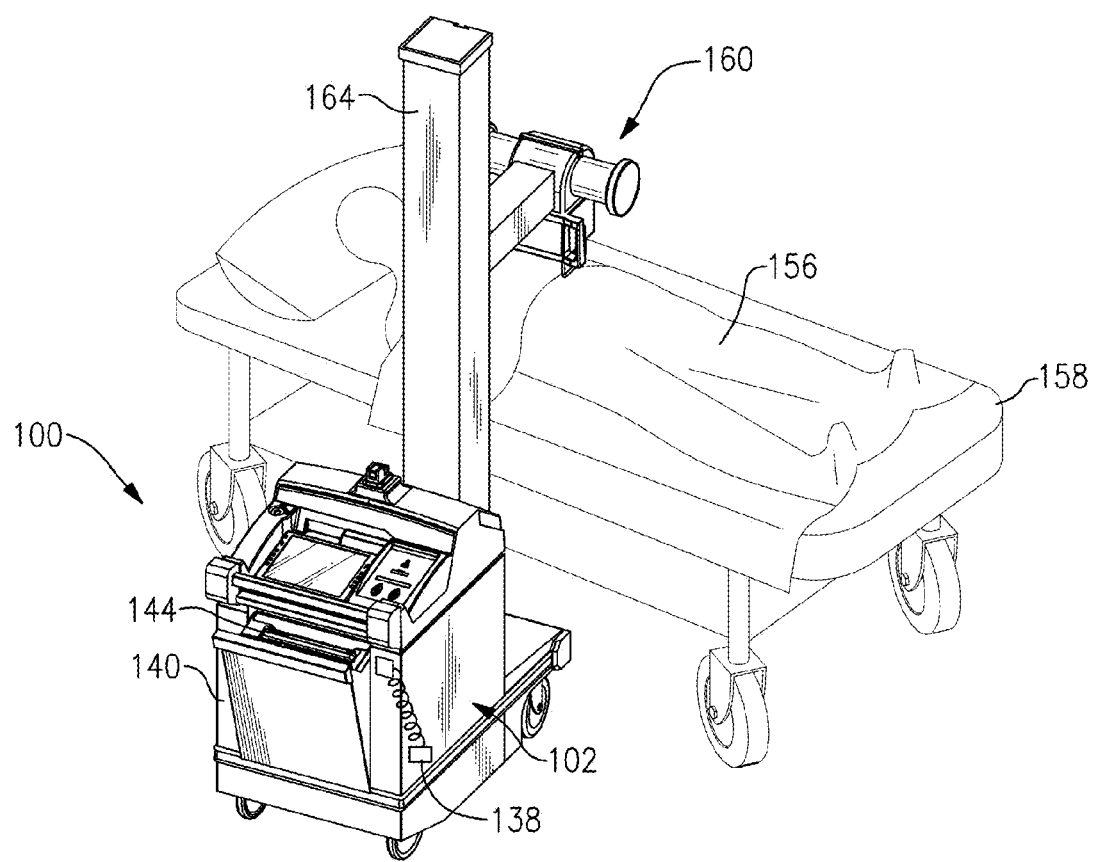
FIG. 3 is a top perspective view of the converted mobile X-ray diagnostic apparatus of FIGS. 1 and 2, as used in a typical examination procedure.
Figure 4:
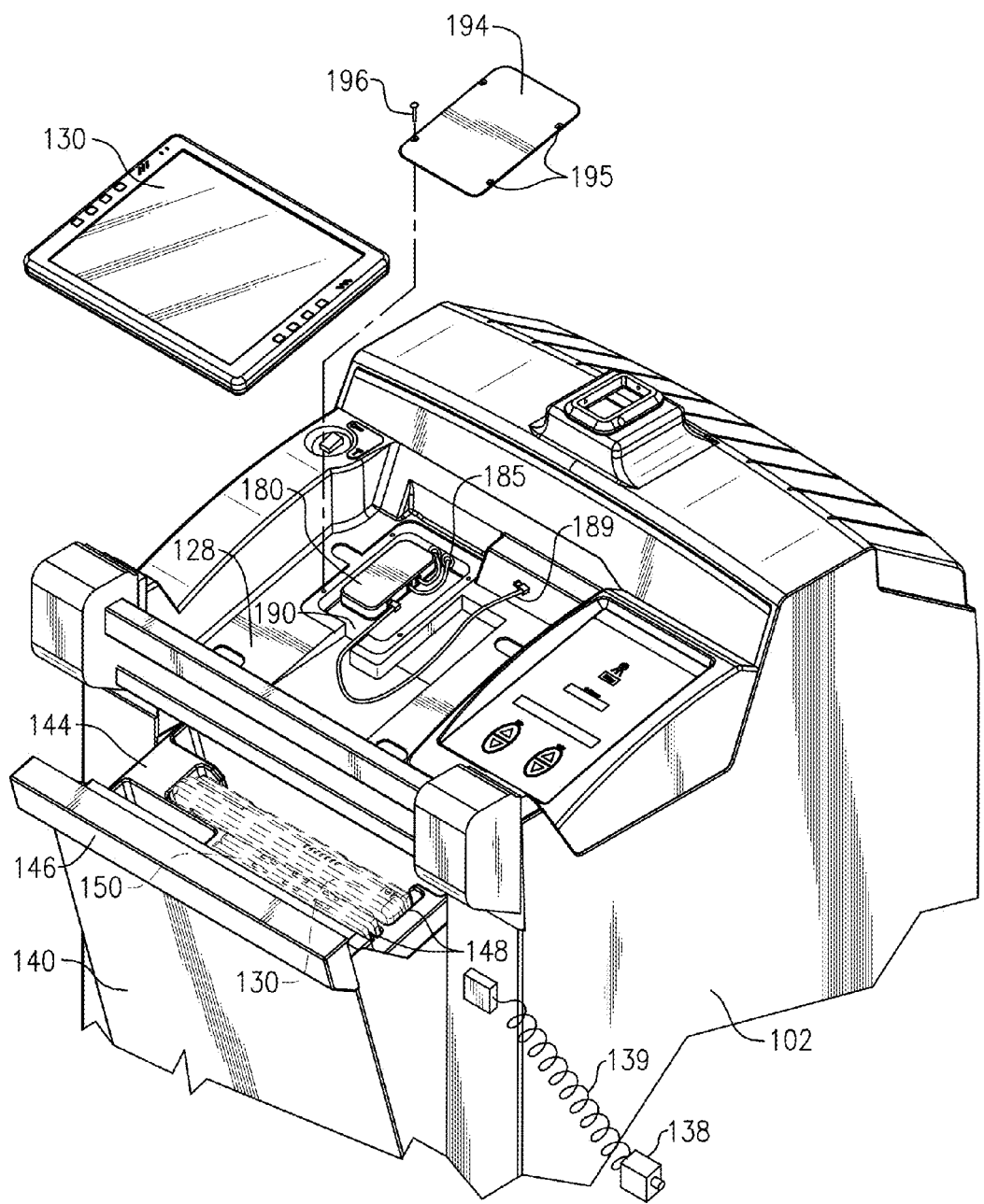
FIG. 4 is an enlarged partial front perspective view of the converted mobile X-ray diagnostic apparatus of FIGS. 1-3.

The front-facing portion of the wheeled cart 102 includes the drawer 140 into which the drawer insert 144 of the digital conversion kit 103 is disposed. Referring to FIGS. 1, 3 and 4, the drawer insert 144 according to this exemplary embodiment is defined by a frame 145 that is sized to be fitted within the drawer 140 and includes a plurality of defined vertically extending slots 148 of varying size and depth that are appropriately sized for retaining at least one digital flat panel X-ray detector 150, as well as the tablet PC 130 for storage therein when each or either is not in use. Each of the foregoing components are shown as stored in phantom in FIG. 3, for the sake of completeness. Additional enclosures can be made to the drawer insert 144, for example, for the storage of additional batteries, cables and other componentry. The drawer 140 of the cart 102, according to this exemplary embodiment, further includes an exterior top handle 146, and is hingably supported at the bottom thereof in proximity of the base portion 108. It should be noted that the drawer 140 provides one suitable means for storage of the foregoing elements, though the substitution of other means should be readily apparent to one of sufficient skill in the field.

Referring to FIG. 2, the wheeled cart 102 includes a set of wheels 120, mounted by conventional means beneath each bottom corner of the base portion 108 of the cart 102, thereby enabling the herein described diagnostic apparatus 100 to be movable between various examination rooms of a medical facility. According to this specific version, two rear wheels 120a each include casters 124, enabling the apparatus 100 to be easily turned and fixed in a specific location, the cart further including a brake and brake release bar 131. In addition, a front handle bar 127 is disposed adjacent the upper end of the wheeled cart 102 in order to facilitate movement by the technician or caregiver, the front handle bar being mounted at a suitably convenient height on the apparatus 100 for ease of use by the X-ray technician or other care or service provider.

Referring to FIGS. 2 and 3, the wheeled cart 102 is equipped with an X-ray generator assembly 160, the generator assembly including a light collimator and an X-ray source that is supported on a vertically disposed support column or post 164 of the cart 102. The foregoing features relating to X-ray generation are well known in the field such as those described for example in U.S. Pat. Nos. 6,702,459 and 5,835,558, each incorporated by reference in relevant part herein. The X-ray generator assembly 160, according to this embodiment, is cantilevered by an arm 168 that is fixedly secured with a vertical slot 166 extending through the center of the support column 164. The X-ray source can be selectively positioned in relation to a patient to be examined using various controls provided on the operator's console on the cover 101, 110 of the cart 102 and in which exposures are taken using the user actuable exposure control switch 138. The support column 164 can be rotated about a base (not shown) by means of the above-noted controls while the cantilevered arm 168 can also be raised and lowered, as needed, so as to move the X-ray generator assembly 160 into a suitable position; for example, relative to a patient gurney 158, as shown in FIG. 3. The herein described mobile X-ray diagnostic apparatus 100 is powered by a plurality of batteries (in this specific version, nine (9) batteries are provided in series) that provide approximately 116 volts at full charge. The batteries are stored within the apparatus portion of the wheeled cart 102 and are accessible as needed, the cart further including an external charging port (not shown).

A discussion now follows relating to the major components of the digital conversion kit 103. The tablet PC 130 according to this exemplary embodiment is sufficiently compact to fit within a recess or receiving cavity that is provided on the replacement cover 110, the tablet PC including a touch screen having a virtual keyboard and also preferably an Ethernet notebook adapter, in addition to a wireless router 152 of the digital conversion kit 103, which is also attached thereto. According to the exemplary embodiment, the tablet PC 130 is a Model J3500 Tablet PC sold by Motion Computing of Austin, Tex., this computer preferably having an extended life battery, touch screen with virtual keyboard. According to the present embodiment, the tablet PC further includes USB connection ports as well as Ethernet connections. In the present embodiment, the tablet PC 130 includes a 10/100 fast Ethernet adapter inserted into an appropriate slot and further be configured for directly interfacing with a wireless access point or as in the present embodiment, using the separately connected wireless router 152, FIG. 5, for enabling same. Additionally and depending on the network peripheral device connectivities, the computer can further include a Firmware port, USB connections for external keyboard or CD/DVD drive, external SATA (e-SATA) for external storage, as well as plugs for headphones and microphone jacks. It will be readily apparent that other suitable compact computing devices (Tablet or notebook PCs) can be utilized having appropriate storage and RAM capacities for storing and running digital image processing software, such as the i5 Imaging Software suite sold by InfiMed, Inc. of Liverpool, N.Y. The specific tablet PC 130 used in this embodiment is equipped with a 160 GB HDD and an Intel Core vPro processor having a display with a pixel density of 1024×768 landscape.

According to this embodiment, the replacement cover 110 is a molded plastic component that is sized to replace the original cover of the wheeled cart. The replacement cover 110 includes a pair of defined receiving cavities 128, 190 sized to releasably retain the tablet PC 130 as well as the means used for diverting the exposure control signal of the user-actuable exposure control switch 138 to the tablet PC. Each of the receiving cavities 128, 190 are defined in an upper surface of the replacement cover 110. The intent of the replacement cover 110 is to provide a receptacle for the tablet PC 130 and exposure control signal diverting means and associated cabling. Otherwise and as described below, the original components and operator controls, such as the key control switch and associated controls for operating the X-ray generator assembly 160 are essentially unchanged and are already included or are reattached onto the replacement cover 110 prior to its attachment to the apparatus 100.

A critical component of the herein described conversion kit 103 is the above-noted means for rerouting or diverting the exposure control signal from the user actuable exposure control switch 138 of the apparatus 100 to the tablet PC 130. According to this exemplary embodiment, the exposure control signal diverting means are in the form of an input/output (I/O) box or device 180 (also referred to throughout this discussion as an "intercept" box) and a replacement digital switch cable 185, shown diagrammatically in FIG. 5. Referring briefly to the detailed electrical schematic diagram provided at FIGS. 6(a) and 6(b), the I/O intercept box 180 is a compact housing that retains a resident microprocessor 182 and includes a set of interface ports 184, 186 that receive the exposure control signal via the replacement digital switch cable 185, the latter being attached to the user actuable exposure control switch 138. The intercept box enables the exposure control signal to still be directed to the X-ray generator assembly 160, but also routed to the tablet PC 130 via a USB port 188 of the I/O intercept box 180. According to this exemplary embodiment, the I/O intercept box 180 is 5" long× 2.5" wide×⅞" thick.

As noted and in standard or typical operation prior to reconfiguration, the mobile analog X-ray diagnostic apparatus 100 is operated by various controls that are disposed on the operator's console of the original cover 101, FIG. 1, of the wheeled cart 102, including the tethered user-actuable exposure control switch 138 used in conjunction with the X-ray generator assembly 160 to emit X-ray radiation of sufficient dosage and duration for a single exposure with regard to a conventional analog film or film cassette (not shown) in a known manner. Each exposure is removed from the examination area in the facility and separately viewed using a light table or other means to determine if a proper image has been taken and to analyze the captured image.

The following discussion relates to conversion of the herein described analog mobile X-ray diagnostic apparatus 100 using the digital conversion kit 103 to enable digital radiographic operation:

For purposes of reconfiguring or converting the analog X-ray diagnostic apparatus 100 for digital radiography and according to this specific embodiment, the original cover 101, FIG. 1, of the mobile apparatus 100 is initially unhinged and removed from the remainder of the wheeled cart 102, after all power to the apparatus 100 has first been disconnected. For purposes of removal, the original cover 101, which is hingeably attached to the upper end of the cart 102, is first lifted to an open or service position and then is locked in place. Specific connections to the analog X-ray diagnostic apparatus 100 provided on the underside of the original cover 101 are then disconnected in order to enable physical disconnection of the original cover from the remainder of the mobile apparatus 100. More specifically and according to this exemplary embodiment, the key switch cable and data cable are each disconnected from the controller display board located on the original cover 101 of the apparatus 100 and the ground cable and the data cable mount are subsequently removed, as well as the key switch cable from the data cable mount of the apparatus 100. Once these connections have been relieved, the original cover 101 can then be completely removed from the remainder of the wheeled cart 102, after the hinged connection to the wheeled cart 102 is also disconnected.

As noted and according to this embodiment, the replacement cover 110 is a molded plastic component which is sized to fit onto the upper portion of the wheeled cart 102. It is the intention that each of the prior removed components be reinstalled onto the replacement cover 110 prior to installing the cover onto the top of the cart 102. That is, the replacement cover 110 is further configured to receive the display board and controller display board, in addition to the key switch that were each previously removed from the original cover 101. Alternatively, the replacement cover 110 can already be separately equipped with any and/or all of the foregoing features though this is a more expensive option, since these components are basically identical to those previously removed.

Therefore and according to this embodiment, the controller display board, the key switch and the display board are each removed from the original cover 101 and subsequently reinstalled onto the replacement cover 110. In addition, the data cable, ribbon cable and a ground cable (if applicable) of the original cart 102 are then each reinstalled between the controller display board and the display board of the apparatus 100.

The digital conversion kit 103 includes a digital switch (exposure control) cable 185 that replaces the existing exposure control switch cable to enable interconnection with the I/O intercept box 180. Typically, the exposure control cable (not shown) provided within the apparatus portion 112, FIG. 2, of the wheeled cart 102 electrically links the user actuable exposure control switch 138 with the X-ray generator assembly 160. The replacement digital switch cable 185, FIG. 5, includes a pair of wire feeds each having pinned connectors on one end that are initially fed through appropriately sized apertures from the underside of the replacement cover 102 into the recess 190, as shown in FIG. 4.

Figure 5:
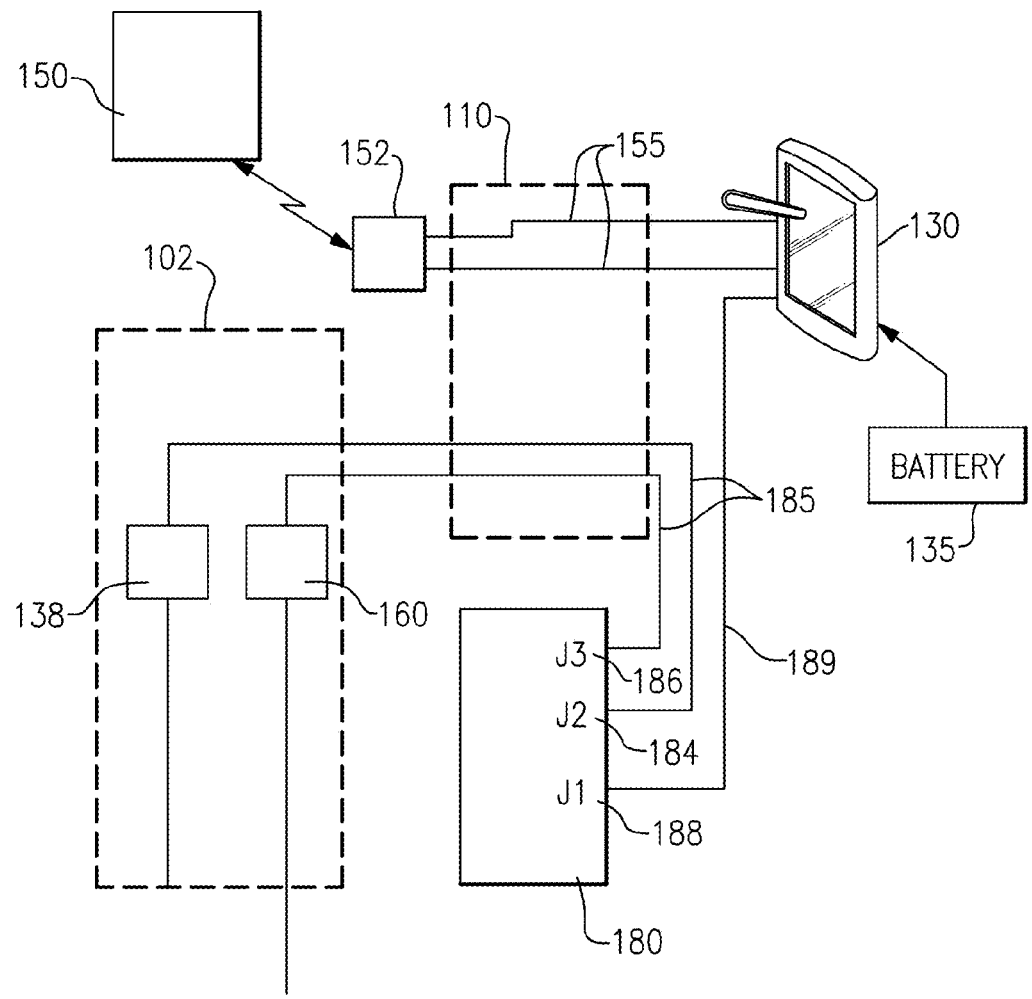
FIG. 5 is a generalized electrical block diagram relating the connectivity of the tablet PC within the converted mobile X-ray diagnostic apparatus of FIGS. 1-4.

In addition and according to one version, a router cable 155, FIG. 5, can also be routed into the aperture and into cavity 190, the router cable also a pair of USB connectors on one side and a power plug for the wireless router 152 on the remaining end, as shown in the schematic of FIG. 5. As discussed below, the wireless router 152 is used in one version in conjunction with the tablet PC 130 to establish wireless communication with a digital flat panel detector 150. The wireless router 152 is attached to the upper surface of the replacement cover 110 by suitable means, such as hook and loop fasteners or other appropriate fastening means. Significantly, the resident battery of the tablet PC 130 provides power to the wireless router 152. As such, the components of the digital conversion kit 103 do not draw power from the X-ray apparatus 100 to otherwise affect X-ray generation.

Figure 6A:
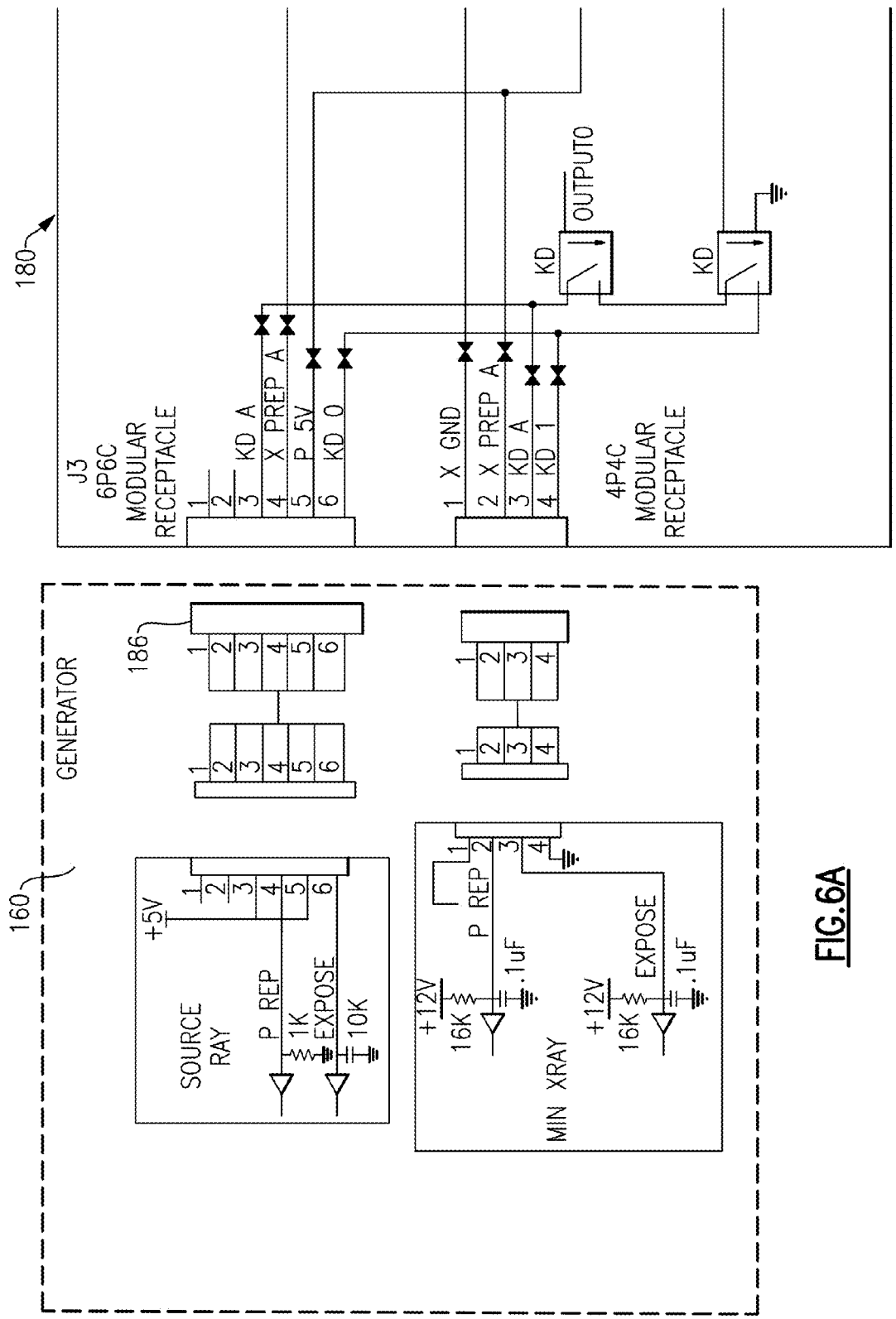
FIGS. 6A and 6B combine to represent a more detailed electrical schematic block diagram of the I/O intercept box as used in the mobile X-ray diagnostic apparatus of FIGS. 1-5.
Figure 6B:
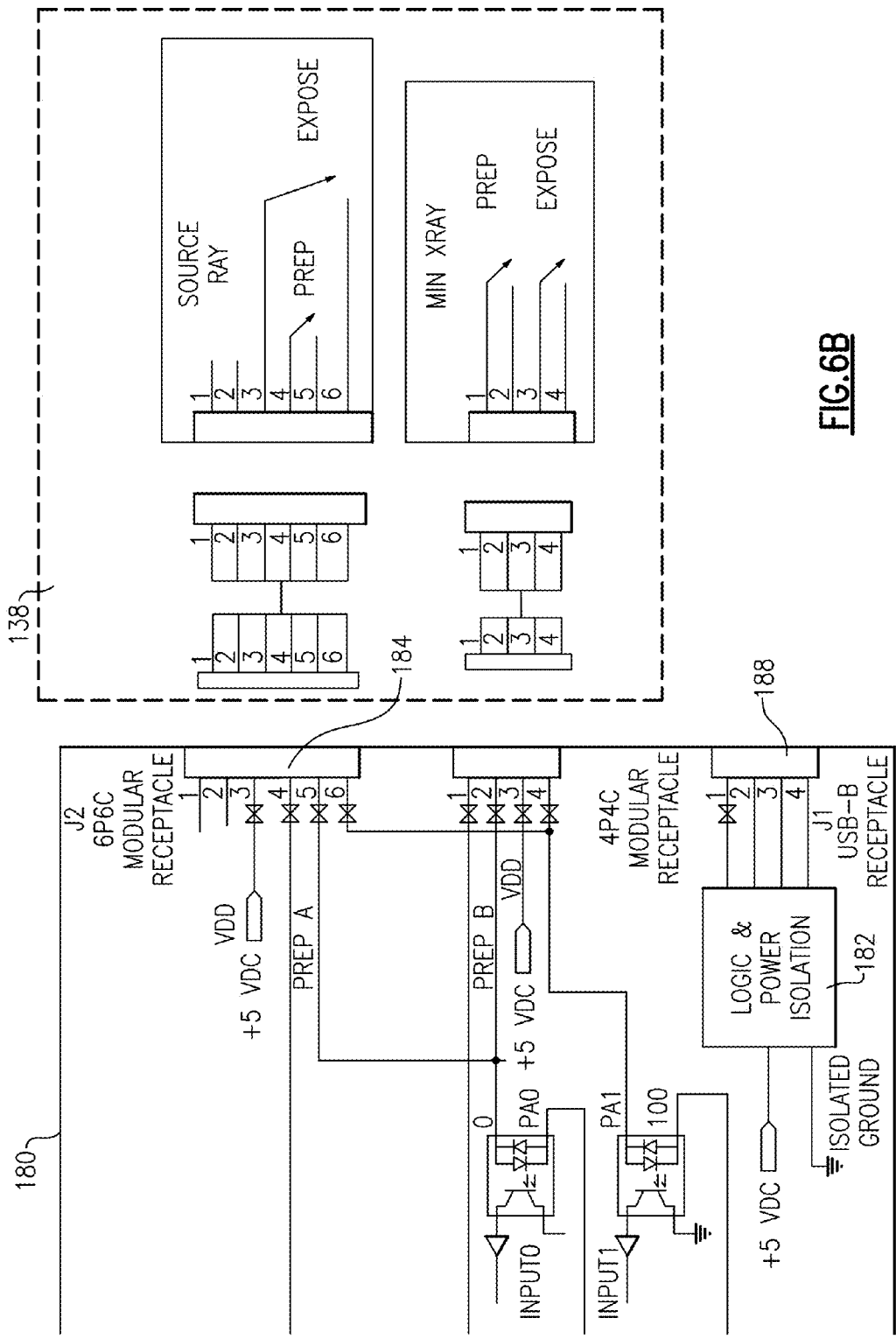
Figure 8:
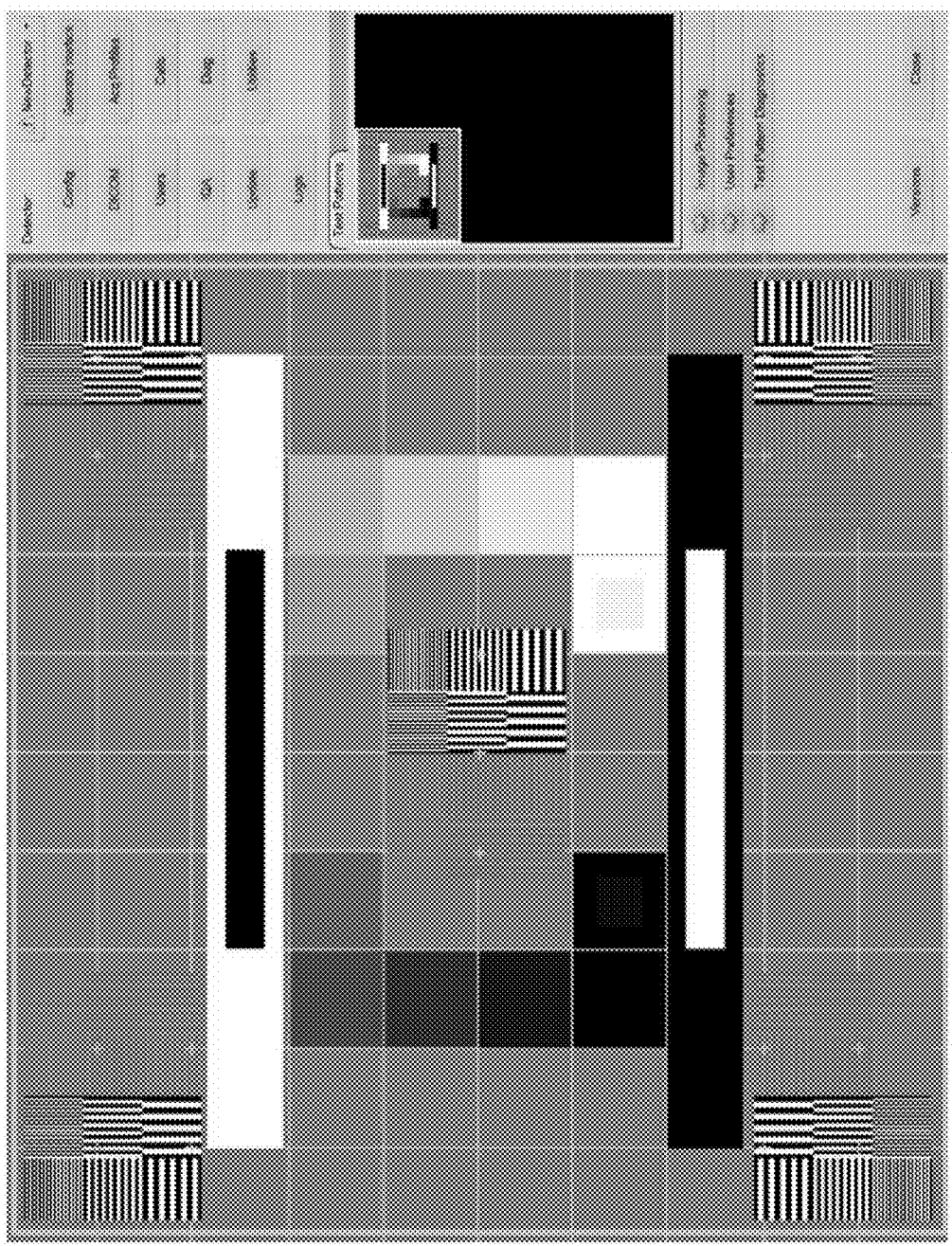
Figure 9:
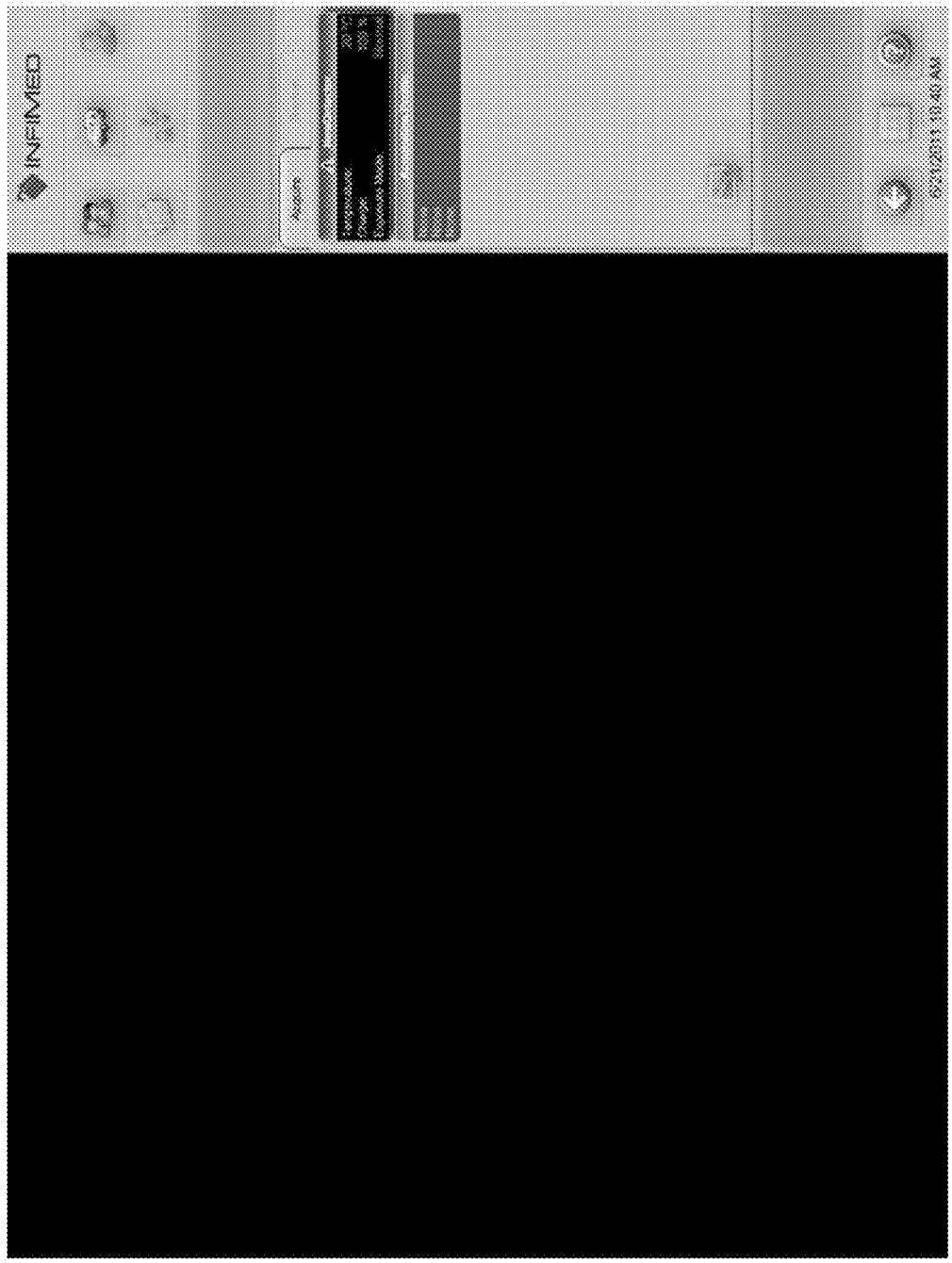
Figure 10:
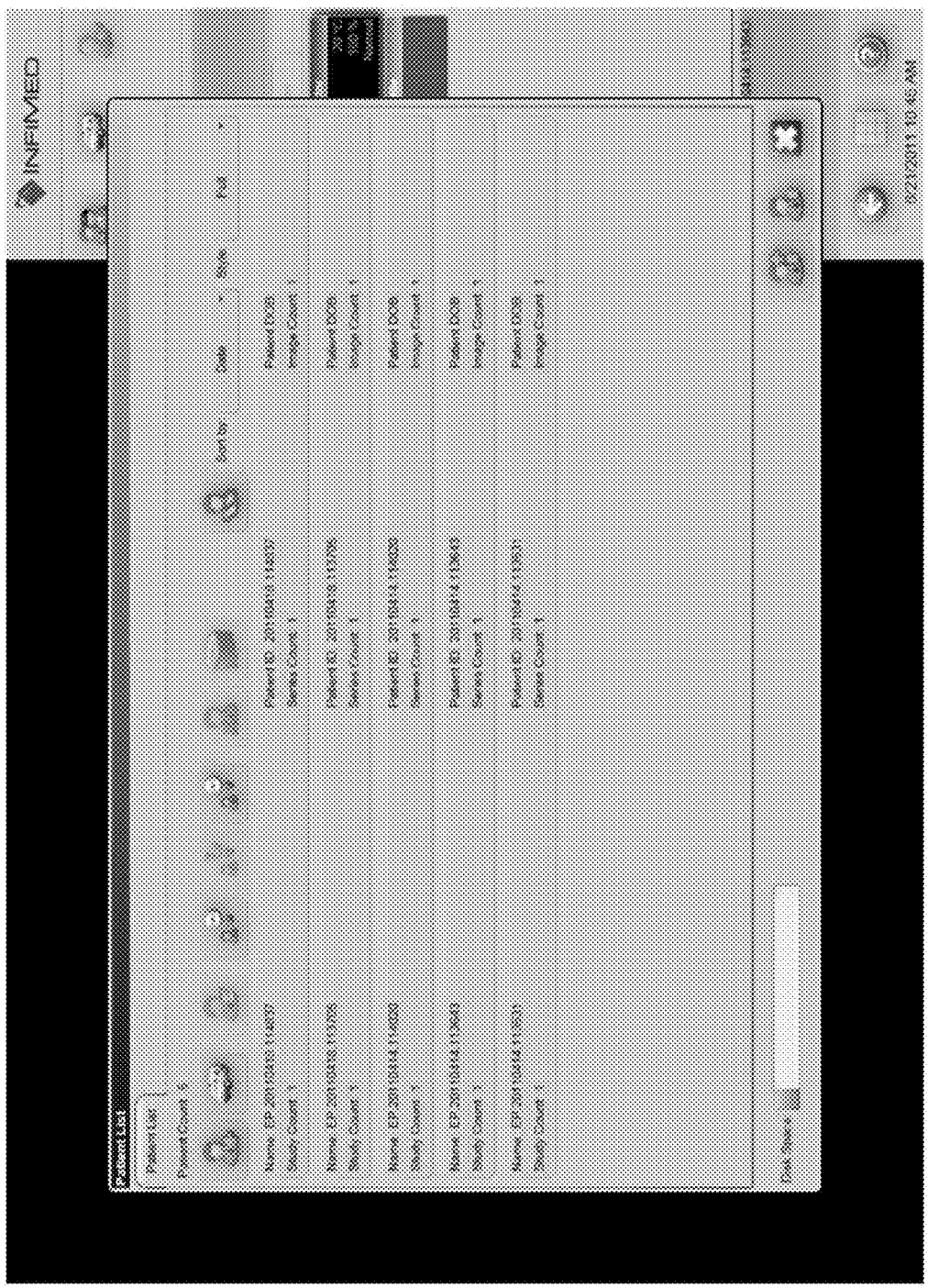
Figure 11:
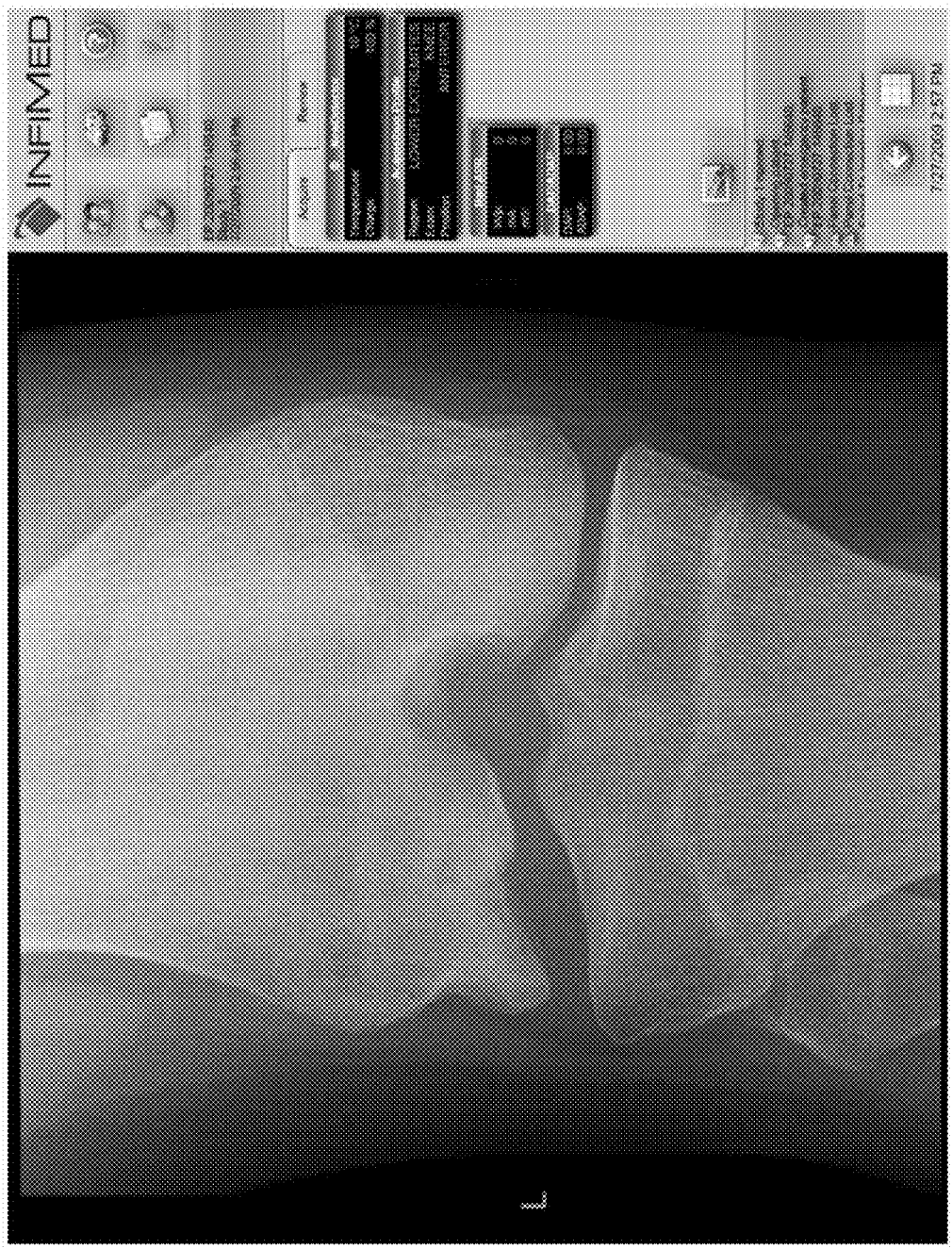
Figure 12:
Figure 13:
Figure 14:
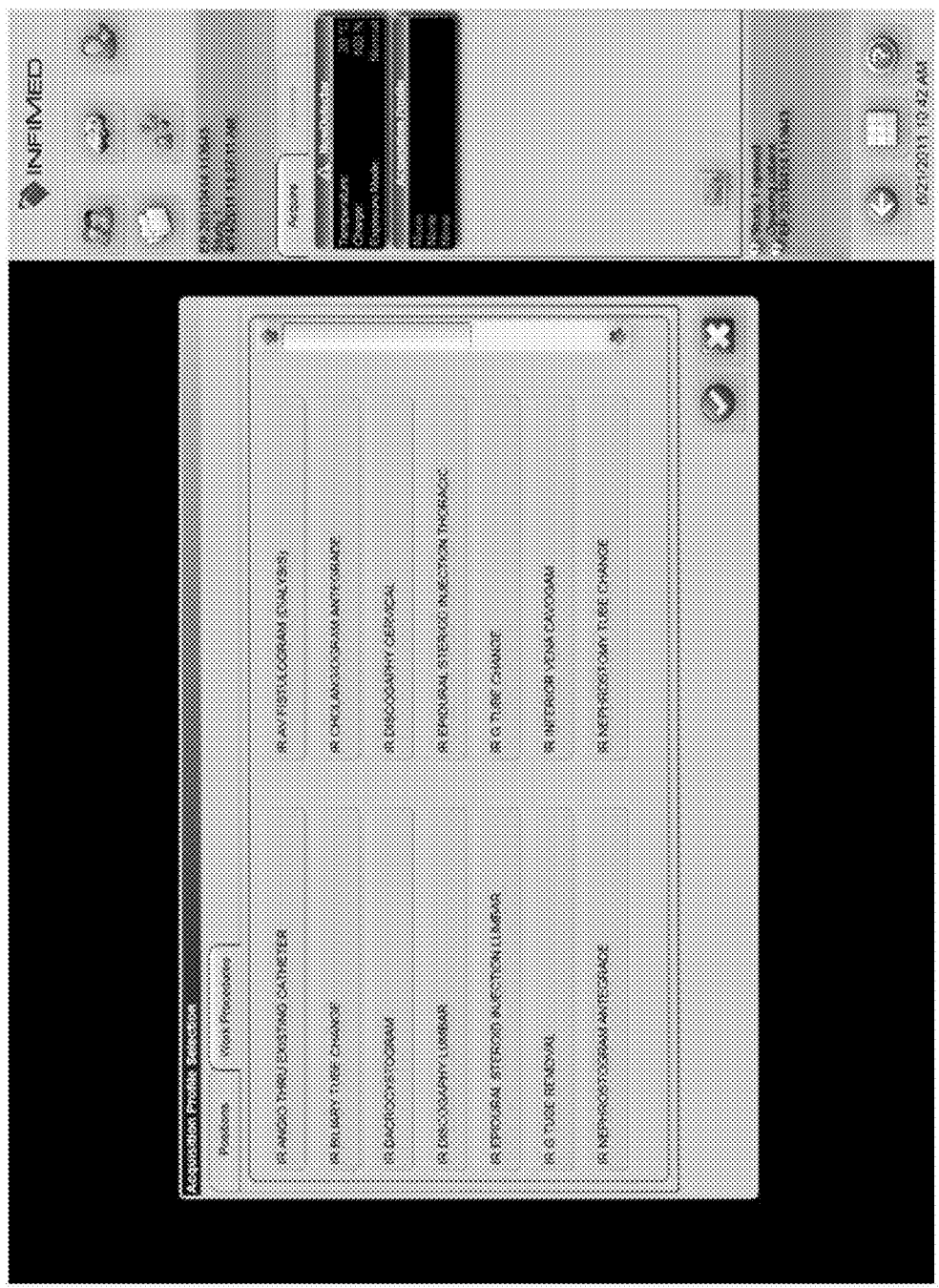

The remaining ends of the replacement digital switch cable 185 are then attached to the appropriate connectors of the user actuable exposure control switch 138 of the apparatus 100 via plug-in connectors on the remaining end of the cable as shown schematically in FIGS. 5 and 6(A), 6(B).

As noted above, the means used to reroute the existing exposure control signal from the user actuable exposure control switch 138 of the apparatus 100 and direct same to the tablet PC 130 is provided in the form of an input/output (I/O) box or device 180 (also referred to throughout this discussion as an "intercept" or "I/O intercept" box). Referring to the detailed electrical schematic diagram provided at FIGS. 6(a) and 6(b), the I/O intercept box 180 is a compact enclosure that retains a resident microprocessor 182 as well as a set of interface ports 184, 186 that enable the exposure controls signal of the apparatus 100 to be intercepted using the distal switch cable 185 and re-routed to the tablet PC 130 via a USB port 188.

The schematic block diagram provided at FIG. 5 illustrates the interconnectivity of the I/O intercept box 180 in regard to the mobile diagnostic apparatus 100 and the tablet PC 130 in accordance with this exemplary embodiment. As described herein, the digital switch cable 185 includes a pair of pinned connectors at one end of the cable that are linked to the ports 184, 186 of the I/O intercept box 180, permitting the signals from the user-actuable exposure control switch 138 to be re-directed to the tablet PC 130. The exposure control signal is transmitted via cabling 189 from the USB port 188 of the I/O intercept box 180, the cable being routed through an aperture in the underside of the replacement cover 110 to the receiving cavity 128 of the replacement cover 110. According to this exemplary embodiment, the I/O intercept box 180 is separately retained within an open-ended enclosure or cavity 190 further embedded within the receiving cavity 128 of the replacement cover 110. The cavity 190 and the I/O intercept box 180 are covered by a retaining plate 194 and secured using a set of threaded fasteners 196 attached through mating holes 195, 197 formed in the retaining plate and replacement cover 110, respectively.

As shown in the Figs and when attached to the apparatus 100 and the I/O intercept box 180, the tablet PC 130 provides a user interface that is fully engageable with the mobile diagnostic X-ray apparatus 100 with the tablet PC being retrofitted in releasable manner within the cavity 128 provided in the upper surface of the replacement cover 110. The tablet PC 130 is attached to one end of the USB cable 189, the remaining end being attached to the I/O intercept box 180 at interface port 188. As shown in the schematic diagrams of FIGS. 5 and 6(a) and 6(b), the I/O intercept box 180 permits the tablet PC 130 to digitally operate the mobile X-ray apparatus 100, but in which the tablet PC is separately powered by means of its resident battery 135 and not drawing any power away from the X-ray generator assembly 160. The tablet PC 180 is disposed according to this version within the receiving cavity 128, which is configured to retain same, but also selectively enables the selective release thereof. In other words, the I/O intercept box 180 provides a connective junction between the tablet PC 130 and the controls of the herein described apparatus 100.

In use, the tablet PC 130 is loaded with digital X-ray image processing software, such as the i5 Imaging Software suite available from InfiMed Inc., of Liverpool, N.Y. This or similar software permits the tablet PC 130 to be used as a user interface in connection with the apparatus 100 in order to control exposures (digital images) of at least one patient, process and review images, and export images as needed to a network or other connected device. Exemplary screen shots are provided in FIGS. 8-15 of the user interface provided by the tablet PC 130 using the digital processing software, illustrating various operational aspects of the tablet PC 130 for purposes of X-ray generation and exposure management of a remotely controlled digital flat panel detector 150, including acquisition and review of various exposures.

As shown in FIG. 7, the releasability of the tablet PC 130 in connection with the mobile diagnostic apparatus 100 provides additional and enhanced versatility for other digital based applications and uses that can realized in a medical facility. First and according to the presently described first mode (A), the tablet PC 130 is used in conjunction with the converted mobile X-ray examination apparatus 100 in the manner previously described with reference to FIGS. 1-6. As previously noted and in this first mode, the tablet PC 130 is releasably disposed within the receiving cavity 128 provided in the replacement cover 110 and is connected via USB cabling 189 with the USB port 188 of the I/O intercept box 180 in order to receive the exposure control signal of the converted apparatus 100. As noted, this signal is re-routed to the tablet PC 130, but otherwise this signal is still also routed to the X-ray generator assembly 160. The tablet PC 130 includes resident software to control the operation of the X-ray generator assembly 160 using the user actuable exposure hand control of the apparatus 100 and acquire and review exposures from the digital flat panel detector 150 through either the tablet PC's internal access point (not shown), the router 152, FIG. 1, or via an Ethernet or other tethered connection, in which the tablet PC is configured for either wired or wireless communication, such that for example video data can be transmitted via the Ethernet connection and using the connected router 152, FIG. 5.

Also and as previously noted the tablet PC 130 and wireless router 152 are each powered using the computer's resident battery 135 and therefore are not required to separately draw or divert electrical power from the mobile diagnostic apparatus 100 in terms of its operation. Therefore and for purposes of conversion thereof, the tablet PC 130 or other aspects of the digital conversion kit 103 do not otherwise interfere with power consumption or the operation of the mobile diagnostic apparatus 100.

Preferably, the tablet PC 130 can be releasably attached and removed from the replacement cover 110 of the present mobile or portable apparatus 100, wherein the mobile apparatus 100 can be reconfigured to again permit analog operation, as needed. This latter reconfiguration capability can be provided by means of disconnecting the intercept box 180 from the wheeled cart 102. Alternatively, the intercept box 180 can be separately enabled for selective operation between digital and analog operational modes, such as by means of a jumper cable assembly (not shown) or a toggle switch (not shown). In a reconfiguration mode, the tablet PC 130 is removed from the receiving cavity 128 of the replacement cover 110. In one version, the digital switch cable connectors are each removed from the I/O intercept box 180 and connected to respective ports of the jumper cable assembly (not shown).

Referring back to FIG. 7, the tablet PC 130 can be releasably removed from the receiving cavity 128 of the replacement cover 110 of the mobile examination apparatus 100, allowing the tablet PC to be separately and alternatively used in a separate (B) mode of operation. According to the depicted example, the tablet PC 130 can be used in conjunction with at least one digital flat panel detector 150 by means of wired or wireless interconnection in order to convert an examination room 230 of a medical facility that was previously configured only for conventional analog (film) X-ray examination.

For purposes of the following discussion, similar parts are herein labeled with the same reference numerals for the sake of clarity. In this latter (B) mode, the tablet PC 130 can be separately connected by means of a wireless router (not shown) with an external wireless access point 240 (or other wireless or wired communication means) provided as part of the tablet PC or more preferably that is suitably disposed within the confines of a examination room 230 and a conventional (i.e., analog) X-ray apparatus, shown herein as 264, along with a flat panel detector 150 in order to convert the examination room and thereby enable digital radiography. The X-ray apparatus 264 can, for example, be a dedicated apparatus that includes an X-ray generator assembly 268 comprising a light collimator and an X-ray source, the apparatus being fixedly attached to fixturing that is provided within the confines of the examination room 230. A docking station 260, disposed exterior to the examination room according to this exemplary embodiment, provides an exemplary means for connecting the tablet PC 130 with the equipment disposed within the examination room. An I/O intercept box 180, like that previously described for use in the mobile diagnostic apparatus 100, FIG. 1, also with associated cabling akin to digital switch cable 185, FIG. 5, is used to intercept the exposure control signal relative to the X-ray generator assembly 268 and bridge the exposure control signal from the user actuated exposure control switch (not shown) to the tablet PC 130. The docking station 260 includes means for mechanically and electrically receiving the tablet PC 130, wherein the docking station is electrically connected to the apparatus 264 in order to control same remotely via the external wireless access point 240 (or alternatively via a wired connection).

In operation, the tablet PC 130 is taken either from the receiving cavity 128 of the mobile cart 102 or from the drawer insert 144, FIG. 3, thereof along with a flat panel detector 150. The tablet PC 130 is then inserted into the docking station 260 and is releasably retained therein. The digital flat panel detector 150 is disposed in relation to the patient within the examination room 230; for example, beneath a patient 156 on a gurney 158 wherein the X-ray generator assembly 268 is suitably positioned relative to the digital flat panel detector in order to acquire images. The exposure control signal from the user actuated exposure central switch (not shown) is routed to the I/O intercept box 180, wherein a USB cable 289 is attached to docking station 260, as extending from an interface port of the I/O intercept box 180, similar to the prior embodiment. As in the preceding embodiment, the tablet PC 130 includes preloaded software, such as the i5 software suite from InfiMed, Inc., of Liverpool, N.Y., enabling operational control of the digital flat panel detector 150. It should be noted that the duality of modes discussed herein is merely one exemplary version; for example, the examination room conversion described herein could be performed separately and in lieu of the wheeled cart conversion described, according to mode (A). In the herein described example, either disconnection of the I/O intercept box 280 or providing a jumper circuit or other switching (toggling) means enables analog and digital modes to be enabled wherein the examination room can be selectively restored to its original analog configuration when the tablet PC 130 is not being used.

PARTS LIST FOR FIGS. 1-15

100 mobile apparatus, X-ray
101 cover, original
102 cart, wheeled
103 conversion kit
104 chassis
108 base section
110 replacement cover
112 apparatus portion
115 user interface
116 housing
120 wheels
120a rear wheels
124 casters
127 front handle bar
128 receiving cavity—tablet PC
130 tablet PC
131 brake release bar
135 extended life battery, tablet PC
138 user actuable exposure control switch
139 cord or wire, tether
140 drawer
144 drawer insert
145 frame
146 exterior top handle
148 slots
150 flat panel detector, digital
152 router, wireless
155 cable, router
156 patient
158 gurney, patient
160 X-ray generator assembly
164 support column or post
166 slot, vertical
168 arm, cantilevered
170 wireless router
180 I/O intercept box
182 microprocessor
184 interface port
185 digital switch cable
186 interface port
188 USB port
189 USB cabling
190 cavity/recess for I/O intercept box
194 plate, retaining
195 holes
196 fasteners
197 holes
230 examination room
240 wireless access point
260 docking station
264 X-ray apparatus
268 X-ray generator
289 USB cable It will be readily apparent from the preceding description that there are several other modifications and variations covering the intended scope of the present invention that will be suggested to those of skill in the art. The following claims, including all equivalents thereof, are intended to cover and define the scope of the invention.

The invention claimed is:

1. A X-ray diagnostic apparatus originally solely configured for analog-based radiography, said diagnostic apparatus including an X-ray generator assembly, an exposure control mechanism for use with X-ray film, and a conversion kit for converting the apparatus from analog to digital operation, said conversion kit including:
 a tablet at said x-ray diagnostic apparatus, and is releasably attached to said apparatus, said tablet providing a user interface configured to allow user control of the X-ray diagnostic apparatus and having software enabling digital radiographic exposure control; and
 circuitry configured for electrically routing an exposure control signal from said exposure control mechanism of said apparatus to said tablet, wherein said tablet is configured to control an exposure of at least one digital flat panel detector in lieu of a film X-ray cassette.

2. The apparatus as recited in claim 1, wherein said tablet includes a resident battery, said resident battery enabling powered operation thereof without otherwise influencing a power supply of said X-ray diagnostic apparatus.

3. The apparatus as recited in claim 1, further comprising a slot sized for housing said tablet when the tablet is attached to said X-ray diagnostic apparatus.

4. The apparatus as recited in claim 1, wherein said circuitry includes an I/O device that routs the exposure control signal from a hand control of said exposure control mechanism to said tablet.

5. The apparatus as recited in claim 1, including means for linking said at least one digital flat panel detector with said tablet, said linking means drawing power from said tablet.

6. The apparatus as recited in claim 1, further comprising a switching mechanism for enabling selective operation between an analog mode and a digital mode of operation.

7. The apparatus as recited in claim 6, wherein said circuitry comprises an I/O device, and said switching mechanism comprises a jumper circuit provided in said I/O device.

8. The apparatus as recited in claim 1, wherein said apparatus includes a wheeled cart having a cover and an operator's console with controls for operating said X-ray generator assembly, said conversion kit including a replacement cover configured for retaining said tablet at said apparatus.

9. A kit for converting a X-ray diagnostic apparatus originally solely configured for analog-based radiography into a digital radiography apparatus, said X-ray diagnostic apparatus including resident circuitry for controlling analog X-ray exposure triggered by a user-actuable exposure control, said conversion kit comprising:
 a tablet having a user interface and software configured for providing digital radiographic exposure control in an imaging procedure that involves a digital flat panel detector;
 a securing mechanism for releasably mounting said tablet at said apparatus; and
 circuitry configured for diverting an exposure control signal from said user-actuated exposure control to said tablet.

10. The conversion kit as recited in claim 9, wherein said tablet is wirelessly connected to said digital flat panel detector.

11. The conversion kit as recited in claim 9, wherein said tablet is powered by at least one resident battery.

12. The conversion kit as recited in claim 11, wherein said tablet does not draw power from said diagnostic apparatus.

13. The conversion kit as recited in claim 9, wherein said tablet is connected by a wired connection to said digital flat panel detector.

14. The conversion kit as recited in claim 9, further including a replacement cover for said apparatus, said replacement cover including at least one recess for retaining said tablet at said apparatus.

15. The conversion kit as recited in claim 9, wherein said tablet includes a virtual keyboard.

16. The conversion kit as recited in claim 9, wherein said circuitry includes an I/O device having ports for receiving the exposure control signal and for directing said signal to a X-ray generator and to said tablet.

17. A method performed by a converted X-ray apparatus obtained by converting a X-ray apparatus originally configured solely for analog-based radiography, said apparatus including an X-ray generator, a resident power supply, and a control for controlling the exposure of X-rays, said method including:
 diverting an exposure control signal from said control to a tablet, said tablet including resident software for controlling the X-ray generator and a digital flat panel detector, wherein the tablet is a part of a conversion kit for converting the X-ray apparatus from analog operation to digital operation, and wherein the tablet is mounted at the x-ray apparatus; and
 controlling an exposure of said digital flat panel detector using said tablet.

18. The method as recited in claim 17, further comprising powering said tablet using a self contained battery and not drawing power from the resident power supply of said apparatus.

19. The method as recited in claim 17, wherein said tablet communicates wirelessly with said flat panel detector.

20. The method as recited in claim 17, wherein said tablet communicates using a wired connection with said flat panel detector.

21. The method as recited in claim 17, further comprising operating said tablet without drawing from the power supply of said diagnostic apparatus.

22. The method as recited in claim 17, wherein said apparatus comprises an I/O device, said I/O device having ports for interconnecting with exposure control leads of said apparatus.

* * * * *